(12) United States Patent
Lowe et al.

(10) Patent No.: US 10,912,740 B2
(45) Date of Patent: Feb. 9, 2021

(54) TREATING HEPATITIS C WITH CANNABIDIOL

(71) Applicants: Henry Lowe, West Indies (JM); Ngeh J. Toyang, Columbia, MD (US)

(72) Inventors: Henry Lowe, West Indies (JM); Ngeh J. Toyang, Columbia, MD (US)

(73) Assignee: Vilotos Pharmaceuticals, Inc., Baltimore, MD (US)

( * ) Notice: Subject to any disclaimer, the term of this patent is extended or adjusted under 35 U.S.C. 154(b) by 0 days.

(21) Appl. No.: 15/880,801

(22) Filed: Jan. 26, 2018

(65) Prior Publication Data

US 2018/0214389 A1  Aug. 2, 2018

Related U.S. Application Data

(60) Provisional application No. 62/451,481, filed on Jan. 27, 2017.

(51) Int. Cl.
| | | |
|---|---|---|
| *A61K 31/05* | (2006.01) | |
| *A61K 36/185* | (2006.01) | |
| *A61P 31/14* | (2006.01) | |

(52) U.S. Cl.
CPC ............ *A61K 31/05* (2013.01); *A61K 36/185* (2013.01); *A61P 31/14* (2018.01); *Y02A 50/30* (2018.01)

(58) Field of Classification Search
CPC .......... A61K 31/05; A61K 31/14; A61P 31/14
See application file for complete search history.

(56) References Cited

FOREIGN PATENT DOCUMENTS

WO   WO 2017/011785   *   1/2017

OTHER PUBLICATIONS

Dorwald (Side Reactions in Organic Synthesis: A Guide to Successful Synthesis Design, Weinheim: Wiley-VCH Verlag.*
Sylvestre et al. Cannabis use improves retention and virological outcomes in patients treated with hepatitis C. (European Journal of Gastroenterology & Hepatology, 2006, 18: 1057-1063).*
Mechoulam & Hanus. Cannabidiol: an overview of some chemical and pharmacological aspects. Part I: chemical aspects. Chemistry and Lipids, 121, 2002, 35-43.*

* cited by examiner

*Primary Examiner* — Anna Pagonakis
(74) *Attorney, Agent, or Firm* — Royal W. Craig; Gordon Feinblatt LLC

(57) ABSTRACT

A cannabinoid-based pharmaceutical composition for the prevention and treatment of pathogenic viruses (particularly those causing hepatic related conditions such as hepatitis B and C), and most particularly for hepatitis C virus (HCV) infection, having a cannabidiol structure or a pharmaceutically acceptable salt thereof. A method for the prevention and treatment of pathogenic viruses (particularly those causing viral hepatic related conditions such as hepatitis B and C), and most particularly for HCV is also disclosed.

16 Claims, 2 Drawing Sheets

TREATING HEPATITIS C WITH CANNABIDIOL

CROSS-REFERENCE TO RELATED APPLICATION(S)

The present application derived priority from U.S. Provisional Patent Application 62/451,481 filed Jan. 27, 2017.

BACKGROUND OF THE INVENTION

1. Field of the Invention

The present invention relates to cannabinoid derivatives and, mom particularly, to cannabis cannabinoid derivatives or the pharmaceutically acceptable salt thereof that may be used in a pharmaceutical composition for preventing and treating pathogenic viruses, particularly viral hepatitis C (HCV).

2. Description of the Background

Viral hepatitis poses a major health problem globally, and if untreated, leads to severe liver damage resulting in liver cirrhosis and cancer. Viral hepatitis is caused by a group of viruses divided into five types (A, B, C, D, and E), and they are primarily known to attach to the liver. [Alter M J. Mast E E, *The Epidemiology Of Viral Hepatitis In The United States*, Gastroenterol Clin North Am; 23:437-55 (1994)] Hepatitis B virus (HBV) and hepatitis C virus (HCV) are the most dangerous and prevalent of the five virus types. [Lemoine M, Eholie S, Lacombe K., *Reducing The Neglected Burden Of Viral Hepatitis In Africa: Strategies For A Global Approach*, J Hepatol 62:469-76 (2015); Ott J J, Stevens G A, Groeger J, Wiersma S T, *Global Epidemiology Of Hepatitis B Virus Infection: New Estimates Of Age-Specific HBsAg Seroprevalence and Endemicity*, Vaccine 30:2212-9 (2012)] Chronic cases of HBV as well as HCV are among the leading causes of liver cirrhosis and hepatocellular carinoma (HCC) in the world. [Tomesello M L, Buonaguro L, Izzo F, Buonaguro F M. *Molecular Alterations In Hepatocellular Carcinoma Associated With Hepatitis B And Hepatitis C Infections*, Oncotarget; 7:25087-102 (2016)] HBV and HCV infections are also implicated in the development of other diseases including lymphoma, diabetes, and atherosclerosis. [Huang Y W, Yang S S, Fu S C, Wang T C, Hsu C K, Chen D S, et al., *Increased Risk Of Cirrhosis And Its Decompensation In Chronic Hepatitis C Patients With New-Onset Diabetes: A Nationwide Cohort, Study*, Hepatology; 60:807-14 (2014); Younossi Z M, Park H, Saab S, Ahmed A, Dieterich D, Gordon S C, *Cost-Effectiveness Of All-Oral Ledipasvir/Sofosbuvir Regimens In Patients With Chronic Hepatitis C Virus Genotype Infection*, Aliment Pharmacol Ther; 41:544-63 (2015)] HBV is the most prevalent type worldwide and the leading cause of HCC in some countries, especially in Asia. [Lavanchy D., *Worldwide Epidemiology Of HBV Infection, Disease Burden, And Vaccine Prevention*, J Clin Virol; 34 Suppl 1:S1-3 (2005)] Despite the fact that great strides have been made in the treatment and prevention of HBV and HCV, the global burden remains a major health problem. Moreover, the risk of drug resistance, combined with the high cost of current therapies, makes it a necessity for more cost-effective therapeutics to be discovered and developed. There is as such a great need to continue to search for new molecules with activity against hepatitis viruses.

The recent surge in interest in medical cannabis has led to interest in evaluating and validating the therapeutic potentials of cannabis and its metabolites against various diseases including viruses. Cannabinoids, terpenes and cannabinoids are all found in cannabis plants. Cannabinoids are known for their antioxidant and anti-inflammatory health benefits and have relevant pharmacological activities such as antidiabetic, antiallergic, antibiotic, antidiarrheal, and exhibit beneficial pharmacological properties against central nervous system (CNS) disease and cancer. Cannabinoids such as THC and Cannabidiol (CBD), and terpenes like myrcene and limonene, also produce a range of effects. Unfortunately much attention on Cannabis is focused on its recreational use as a psychoactive drug. However, CBD is a nonpsychoactive cannabinoid credited for several pharmacological properties. It is known to have beneficial effects against inflammation/pain, neurological conditions, cancer, and other ailments. [Campos A C, Fogaça M V, Sonego A B, Guimarães F S., *Cannabidiol, Neuroprotection And Neuropsychiatric Disorders*, Pharmacol Res 112:119-27 (2016); Fernández-Ruiz J, Sagredo O, Pazos M R, Garcia C, Pertwee R, Mechoulam R et al., *Cannabidiol For Neurodegenerative Disorders: Important New Clinical Applications For This Phytocannabinoid?*, Br J Clin Pharmacol 75:323-33 (2013); Mechoulam R, Peters M, Murillo-Rodriguez E, Hanus L O., *Cannabidiol—Recent Advances*, Chem Biodivers 4:1678-92 (2007); McPartland J M, Russo E B., *Cannabis And Cannabis Extracts: Greater Than The Sum Of Their Parts?*, J Cannabis Ther 1:103-32 (2012)].

Most of the studies on CBD and Cannabis, in general, have focused on the neuroprotective as well as anti-inflammatory properties. Cannabis was reported to be used as an accompanying remedy by HIV/AIDS patients to alleviate neuropathic pain, wasting, nausea, and vomiting. [anonymous mail survey, J Cannabis Ther 1:35-41 (2001); Prentiss D, Power R, Balmas G, Tzuang G, Israelski D M., *Patterns Of Marijuana Use Among Patients With HIV/AIDS Followed In A Public Health Care Setting*, J Acquir Immune Defic Syndr 35:38-45 (2004); Mukhtar M, Arshad M, Ahmad M, Pomerantz R J, Wigdahl B, Parveen Z, *Antiviral Potentials Of Medicinal Plants*, Virus Res 131:1 (2008)] Other studies have focused on the effects of Cannabis use on patients undergoing treatment for HCV with mixed results. [Sylvestre D L, Clements B J, Malibu Y., *Cannabis Use Improver Retention And Virological Outcomes In Patients Treated For Hepatitis C*, Eur J Gastroenterol Hepatol 18:1057-63 (2006); Ishida J H, Peters M G, Jin C, Louie K, Tan V, Bacchetti P, et al., *Influence Of Cannabis Use On Severity Of Hepatitis C Disease*, Clin Gastroenterol Hepatol 6:69-75 (2008)] However, little is known about the antiviral activity of Cannabis and its CBD. Indeed, current literature draws no correlation.

Given the increasing use and application of medical Cannabis and especially its nonpsychoactive metabolite CBD, the present inventors have validated the therapeutic properties of CBD and have proven efficacy against HCV by various pharmacologic assays.

SUMMARY OF THE INVENTION

It is, therefore, an object of the invention to provide a pharmaceutical composition for the prevention and treatment of pathogenic viruses, particularly viral hepatitis C (HCV) that is a natural or synthetic cannabidiol (CBD) molecule.

It is another object to provide a method for the prevention and treatment of HCV using CBD.

It is still another object to provide a method for synthesizing said specific cannabis-based cannabinoid pharmaceutical compositions.

In accordance with the foregoing objects, the present invention provides a cannabinoid-based pharmaceutical composition for the prevention and treatment of pathogenic viruses (particularly those causing hepatic related conditions such as hepatitis B and C), and most particularly for hepatitis C virus (HCV) infection, having the structure of the general formula of FIG. 1 or a pharmaceutically acceptable salt thereof, and the specific formula of FIG. 2 or a pharmaceutically acceptable salt thereof.

A method for the prevention and treatment of pathogenic viruses (particularly those causing viral hepatic related conditions such as hepatitis B and C), and most particularly for HCV is also disclosed using the specific cannabis-based cannabinoid pharmaceutical compositions above.

BRIEF DESCRIPTION OF THE DRAWINGS

Other objects, features, and advantages of the present invention will become more apparent from the following detailed description of the preferred embodiments and certain modifications thereof when taken together with the accompanying drawings in which.

DETAILED DESCRIPTION OF THE PREFERRED EMBODIMENTS

Reference will now be made in detail to preferred embodiment of the present invention, examples of which are illustrated in the accompanying drawing.

The present invention is a group of cannabis-based cannabinoid pharmaceutical composition useful for the prevention and treatment of certain pathogenic viruses (particularly those causing hepatic related conditions such as hepatitis B and C), and most particularly for hepatitis C virus (HCV) infection by interaction with the CB2 receptor and as such using a host mechanism to indirectly slow the pathogenic process of the HCV virus.

Figure 1:
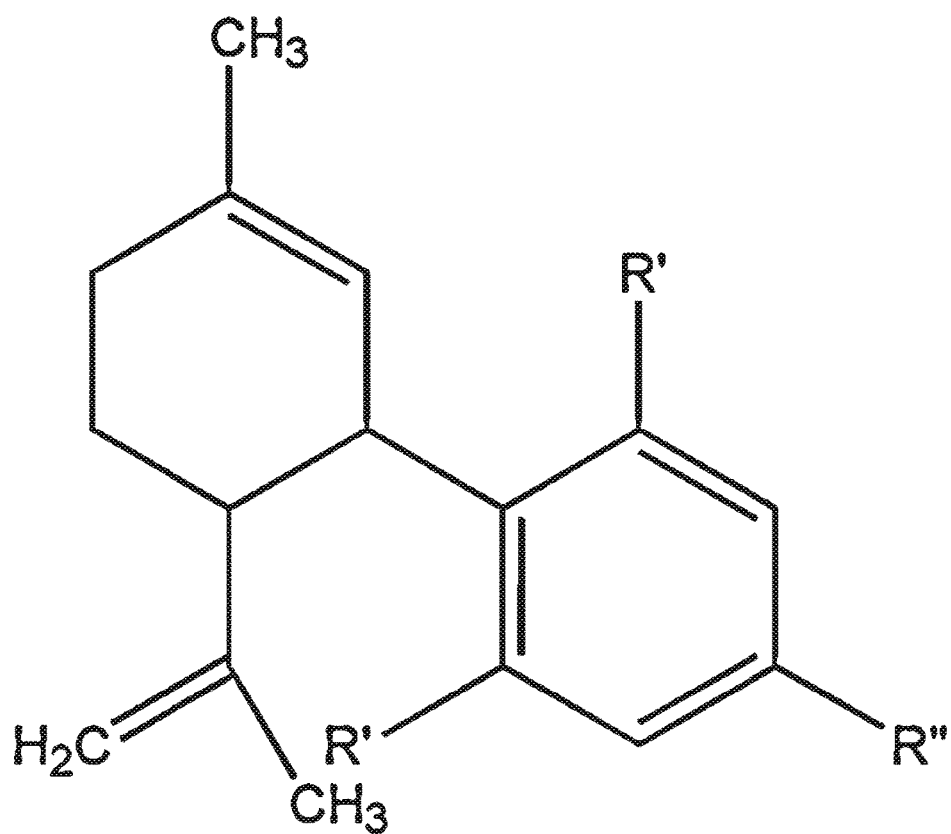
FIG. 1 is an illustration of the general cannabis-based cannabinoid pharmaceutical compositions according to the present invention.

The cannabis-based cannabinoid pharmaceutical composition for the prevention and treatment of diseases has the structure of the general formula of FIG. 1 or a pharmaceutically acceptable salt thereof, in which R' stands for any of the following groups: H, OH, $CH_3$, $OCH_3$ and R" stands for either i) a straight or branched alkyl of 5 to 12 carbon atoms; ii) a group —O—R", where R" is a straight or branched alkyl of 5 to 9 carbon atoms, or a straight or branched alkyl substituted at the terminal carbon atom by a phenyl group; iii) a group —$(CH_2)_n$—O-alkyl, where n is an integer from 1 to 7 and the alkyl group contains 1 to 5 carbon atoms. There are many cannabinoid-type compounds that are psychoactive, but this is undesired for this purpose and so the molecule of the present invention is non-psychoactive.

Figure 2:
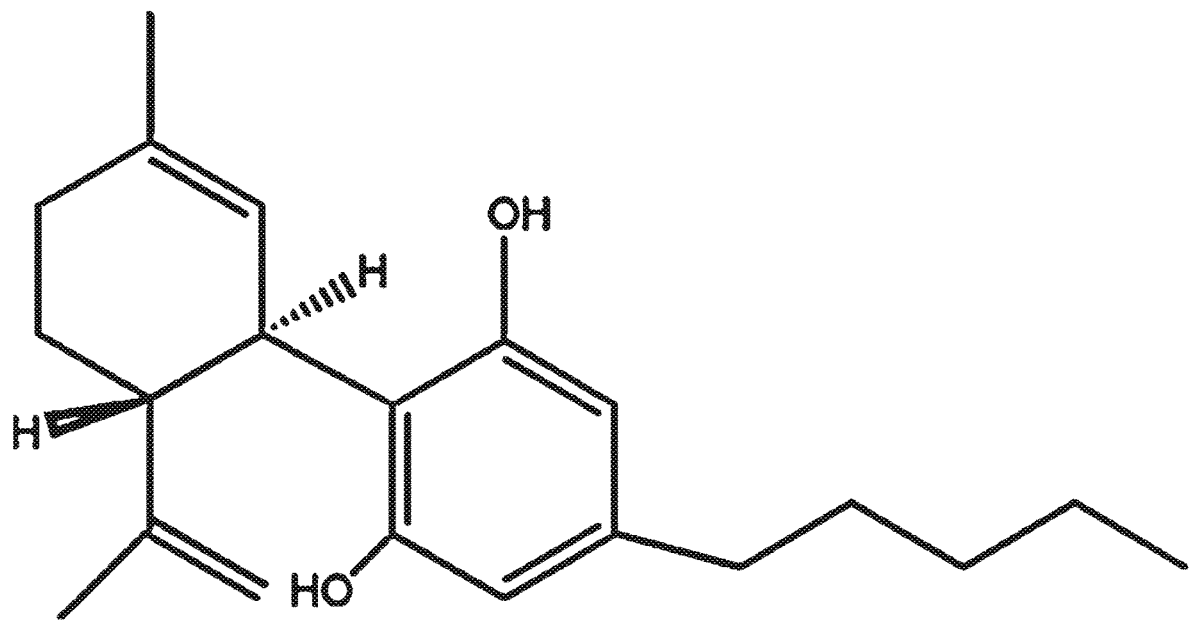
FIG. 2 is an illustration of the specific optimal cannabis-based cannabinoid pharmaceutical composition according to the present invention.

In an embodiment, the pharmaceutical composition for the prevention and treatment of HBV infection has the structure of the specific formula of FIG. 2 or a pharmaceutically acceptable salt thereof. FIG. 2 is a cannabinoid, and more specifically represents the skeletal formula of Cannabidiol.

A method for the prevention and treatment of hepatic disorders using the specific cannabis-based cannabinoid pharmaceutical compositions above is also disclosed. Administration may be by various routes including oral, rectal or intravenous, epidural muscle, subcutaneous, intrauterine, or blood vessels in the brain (intracereboventricular) injections. The cannabinoid derivatives of the general formula (FIG. 1) according to the present invention and a pharmaceutically acceptable salt thereof may be administered in an effective dose, depending on the patient's condition and body weight, extent of disease, drug form, route of administration, and duration, of a pharmaceutically-effective amount within a range of from 0.1 to 500 mg between 1-6 times a day. Of course, most dosages will be by a carrier. The specific dose level and carrier for patients can be changed according to the patient's weight, age, gender, health status, diet, time of administration, method of administration, rate of excretion, and the severity of disease.

The composition may be formulated for external topical application, oral dosage such as powders, granules, tablets, capsules, suspensions, emulsions, syrups, aerosols, suppositories, or in the form of a sterile injectable solution. Acceptable carriers and excipients may comprise lactose, dextrose, sucrose, sorbitol, mannitol, xylitol, erythritol, maltitol, starches, gum acacia, alginate, gelatin, calcium phosphate, calcium silicate, cellulose, methyl cellulose, microcrystalline cellulose, polyvinylpyrrolidone, water, methyl benzoate, propyl benzoate, talc, magnesium stearate, and mineral oil.

Bioactivity of the above-described compounds has been verified by use of in vitro infectious anti-hepatitis assays to determine the effect of the cannabis cannabinoids in the onset and progression of viral hepatitis.

Anti-Hepatitis B Assay

The pure cannabis cannabinoid CBD of FIG. 2 was subjected to a modified anti-hepatitis B assay. [Korba B E, Gerin J L, *Use Of A Standardized Cell Culture Assay To Assess Activities Of Nucleoside Analogs Against Hepatitis B Virus Replication*, Antiviral Res, 19:55-70 (1992); Korba B E, Milman G., *A Cell Culture Assay For Compounds Which Inhibit Hepatitis B Virus Replication*, Antiviral Res 1991; 15:217-28]. The modifications allowed use in real time quantitative polymerase chain reaction (PCR) (TaqMan) to measure extracellular HBV DNA copy number associated with virions released from HepG2 2.2.15 cells. The HepG2 2.2.15 cell line is a stable cell line producing high levels of the wild-type ayw1 strain of HBV. Antiviral compounds blocking any later step of viral replication such as transcription, translation, pregenomeencapsidation, reverse transcription, particle assembly, and release can be identified and characterized using this cell line. In brief, HepG2 2.2.15 cells are plated in 96-well microtiter plates. Only the interior wells were utilized to reduce "edge effects" observed during cell culture; the exterior wells were filled with complete medium to help minimize sample evaporation. After incubation with 5% CO2 atmosphere at 37° C. for 16-24 h, the confluent monolayer of HepG2 2.2.15 cells was washed and the medium was replaced with complete medium containing test compounds at a single concentration of 10 μM. Three days later, the culture medium was replaced with fresh medium and test compounds at a single concentration of 10 μM. Six days following the initial administration of the test compounds, the cell culture supernatant was collected, treated with pronase and DNAse, and then used in a real-time quantitative TaqMan PCR assay. Antiviral activity was determined by calculating the reduction in HBV DNA levels compared to untreated virus control samples. Compound cytotoxicity was determined using MTS (CellTiter 96 Reagent, Promega) to measure cell viability as described above. Results are described below.

Anti Hepatitis C Activity Assay

Huh7.5 cells are grown in Dulbecco's modified essential media (DMEM), 10% fetal bovine serum (FBS), 1% penicillin-streptomycin (pen-strep), 1% Non-essential amino acids (NEAA) in a 5% $CO_2$ incubator at 37° C. Huh7.5 cells were seeded at $1 \times 10^4$ cells per well into 96-well plates according to Southern Research Institute standard format. The test article was serially diluted with DMEM plus 5% FBS. The diluted compound in the amount of 50 µl was mixed with equal volume of cell culture-derived HCV (HCVcc), then applied to appropriate wells in the plate. Human interferon alpha-2b (rIFNα-2b) was included as a positive control compound. After 72 hr incubation at 37° C., the cells were lysed for measurement of luciferase activity using Renilla Luciferase Assay System (Promega) according to manufacturer's instruction. The number of cells in each well were determined by CytoTox-1 reagent (Promega). Test articles were tested with 6 serial dilution in triplicate to derive, if applicable, $IC_{50}$ and $IC_{90}$ (concentration inhibiting HCVcc infectivity by 50% and 90%, respectively), $TC_{50}$ (concentration decreasing cell viability by 50%) and SI (selective index: $TC_{50}/IC_{50}$) values. In the replicon assay, Sub-confluent cultures of the ET line were plated out into 96-well plates that are dedicated for the analysis of cell numbers (cytotoxicity) or antiviral activity and the next day drugs were added to the appropriate wells. Cells were processed 72 hours later when the cells were still sub-confluent. After six half-log serial dilutions of the compound, the applicable EC50 (concentration inhibiting HCV replicon by 50%), EC90 (concentration inhibiting HCV replicon by 90%), IC50 (concentration decreasing cell viability by SP/o) and SI (selective index: EC50/IC50) values were derived. HCV replicon levels are assessed as replicon derived Luc activity. The toxic concentration of drug that reduced cell numbers was assessed by the Cyto-Tox-1 cell proliferation assay (Promega), a fluorometric assay of cell numbers (and cytotoxicity). [Pietschmann, T., V. Lohmann, A. Kaul, N. Krieger, G. Rinck, G. Rutter, D. Strand, and R. Bartenschlager, *Persistent And Transient Replication Of Full-Length Hepatitis C Virus Genomes In Cell Culture*, J. Virol. 76:4008-4021 (2002). Results are described below.

Assay Results

The bioactivity of CBD against HBV and HCV is shown in Tables I and 2 below. Generally, the inventors have found that CBD is active against HCV but not against HBV in vitro. CBD inhibited HCV replication by 86.4% at a single concentration of 10 µM with $EC_{50}$ of 3.163 µM in a dose-response assay. These findings suggest that CBD can be used therapeutically against HCV.

TABLE 1

Inhibitory effect of cannabidiol against viral hepatitis B and C at a single dose of 10 (uM)

| Hepatitis virus | Molecule | Percentage virus inhibition | % cytotoxicity |
|---|---|---|---|
| HBV (pM) | CBD (10) | 0 | 65.7 |
|  | Lamivudine (2) | 97.7 | 0 |

TABLE 1-continued

Inhibitory effect of cannabidiol against viral hepatitis B and C at a single dose of 10 (uM)

| Hepatitis virus | Molecule | Percentage virus inhibition | % cytotoxicity |
|---|---|---|---|
| HCVcc | CBD (10 IiM) | 84.6 | 2.7 |
|  | IFN-a (10 IU/mL) | 85.4 | 22.6 |

HBV: Hepatitis B virus;
HCV: Hepatitis C virus;
HCVcc: Cell culture-derived HCV;
IFN-α: Interferon-alpha;
CBD: Cannabidiol

TABLE 2

Determination of $EC_{50}$ and $CC_{50}$ of cannabidiol against hepatitis C virus

|  | $ES_{50}$ (uM) | $CC_{50}$ (uM) | SI |
|---|---|---|---|
| Sofosbuvir | 0.055 ± 0.0104 | >10 | >181 |
| CBD | 3.163 ± 0.133 | 15.670 ± 0.250 | 4.954 |

CBD: Cannabidiol

Generally, CBD inhibited HCV replication by 86.4% at a single concentration of 10 µM. The compound was not active against the HBV virus in vitro but exhibited a significant cytotoxicity against HepG2 2.2.15 cells which were used to culture the virus. In the HCV assay, CBD inhibited the virus with minimal toxicity against the Huh7.5 cells that were used to culture the virus. Lamivudine and interferon alpha were used as positive controls against HBV and HCV, respectively, and they significantly inhibited viral replication at the single-dose assay. CBD was found to exhibit a dose-dependent inhibition of the HCV virus in the dose-response assay (Table 2). The direct antiviral activity of CBD against HCV indicates that the molecule has an effect against both the viral and nonviral hepatitis, otherwise known as autoimmune hepatitis. Autoimmune hepatitis is an inflammatory liver condition elicited by activated T-cells and macrophages. Studies have shown that CBD by interacting with the CB2 receptor induces apoptosis in thymocytes and splenocytes inhibiting the proliferation of T-cells and macrophages which are responsible for either attacking liver cells or inducing the release of pro-inflammatory cytokines that cause autoimmune hepatitis in the liver. [Tahamtan A, Tavakoli-Yaraki M, Rygiel T P, Mokhtari-Azad T, Salimi V., *Effects Of Cannabinoids And Their Receptors On Viral Infections*, J Med Virol 88:1-12 (2016); Rieder S A, Chauhan A, Singh U, Nagarkatti M, Nagarkatti P., *Cannabinoid-Induced Apoptosis In Immune Cells As A Pathway To Immunosuppression*, Immunobiology 215:598-605 (2010); Nagarkatti P S, Nagarkatti M., U.S. Pat. No. 8,242,178]. CB2 receptors are expressed in immune and immune-derived cells and their activation is known to influence viral infections by altering host immune response, particularly inflammation. [Tahamtan et al., supra] CB2 receptor activation is as such known to suppress inflammation and modulate immune responses to viral infection. [Correa F, Mestre L, Docagne F, Guaza C., *Activation Of Cannabinoid CB2 Receptor Negatively Regulates IL-12p40 Production In Murine Macrophages: Role Of IL-10 And ERK1/2 Kinase Signaling*. Br J Pharmacol 145:441-8 (2005) Rom S, Persidsky Y., *Cannabinoid Receptor 2: Potential Role In Immunomodulation And Neuroinflammation*, J Neuroinmune Pharmacol 8:608-20 (2013)] Host inflammation is also said to be able to drive the progression of HBV and other viral infections where host inflammation is pathogenic and activation of the CB2 would as such be useful in the control of the HBV virus infection since it results in an anti-inflammatory effect. [Reiss C S., *Cannabinoids And Viral Infections*, Pharmaceuticals (Basel); 3:1873-86 (2010)] The benefit of CBD in alleviating liver fibrosis, which is one of the outcomes of untreated viral hepatitis, was also demonstrated in previous studies. [Lim M P, Devi L A, Rozenfeld R., *Cannabidiol Causes Activated Hepatic Stellate Cell Death Through A Mechanism Of Endoplasmic Reticulum Stress-Induced Apoptosis*, Cell Death Dis. 2:e170 (2011)] The studies revealed that one of the most critical cellular events in the development and progression of liver fibrosis is the activation of hepatic stellate cells (HSCs), and CBD was shown to induce apoptosis in activated HSCs by interaction with the endoplasmic reticulum. [Lim et al., supra]

Extraction/Isolation

Figure 3:
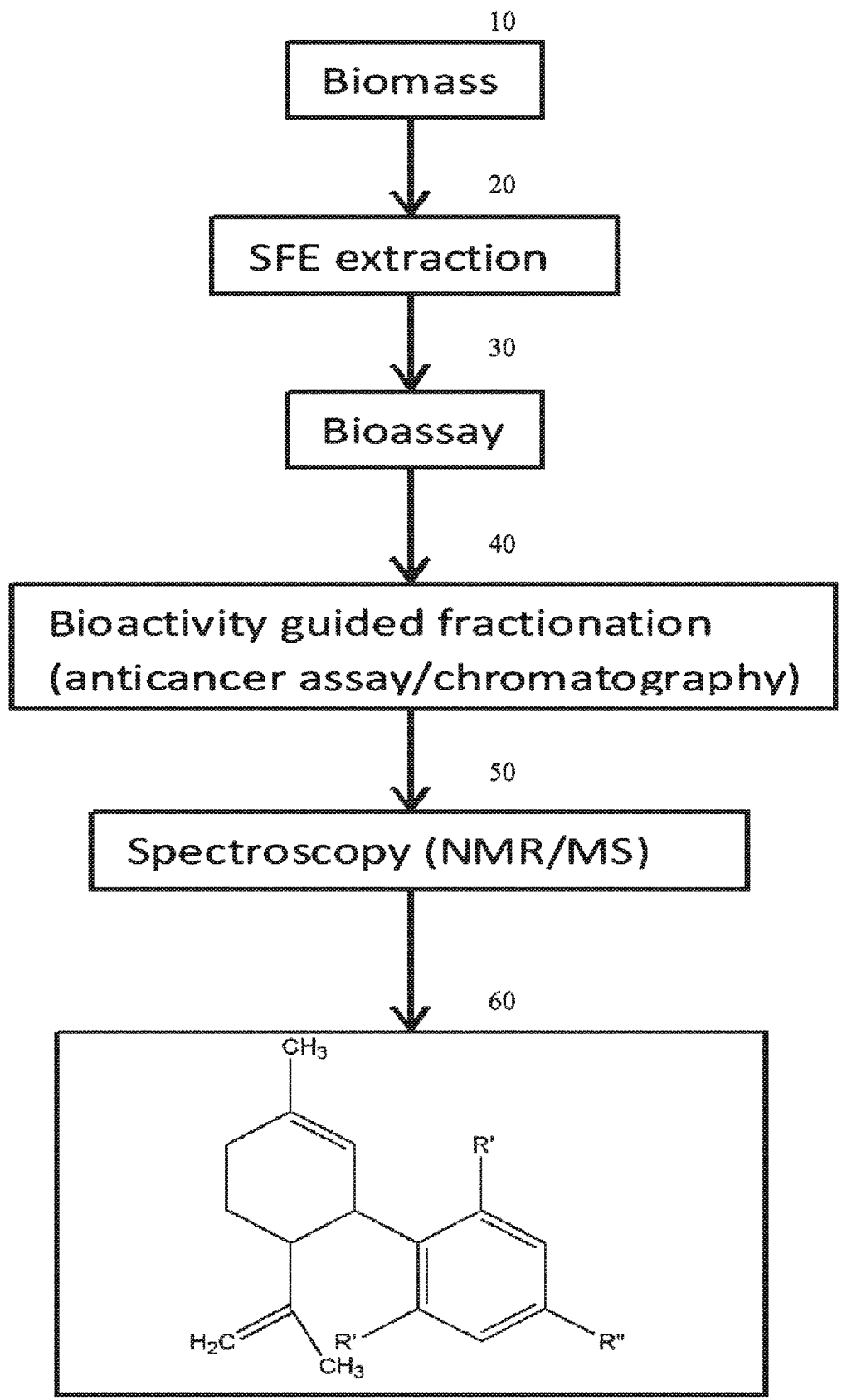
FIG. 3 is a flow diagram illustrating a suitable method for isolating the specific cannabis-based cannabinoid pharmaceutical CBD composition from raw plant material.

A method for isolating the specific cannabis-based cannabinoid pharmaceutical compositions from raw plant material is also disclosed. The isolation was realized according to the scheme shown in FIG. 3.

At step 10 an appropriate amount of plant biomass is collected. For present purposes, Cannabis sativa plants were collected by hand. See, Radwan, M. M., ElSohly, M. A., Slade, D., Ahmed, S. A., Wilson, L., El-Alfy, A. T., Khan, I. A., Ross, S. A., 2008a. Non-cannabinoid constituents from a high potency Cannabis sativa variety. Photochemistry 69, 2627-2633 and Radwan, M. M., Ross, S. A., Slade, D., Ahmed, S. A., Zulfiqar. F., ElSohly, M. A., 2008b. Isolation and characterization of new cannabis constituents from a high potency variety. Planta Med. 74, 267-272. The collected plant material was air dried under shade and pulverized into powder.

At step 20 the powder is subjected to supercritical fluid extraction (SFE) by which carbon dioxide ($CO^2$) is used for separating one component (the extractant) from another (the matrix). The extract is evaporated to dryness resulting in a green residue.

At step 30, for experimental purposes, a bioassay-guided fractionation was employed, using a standard protocol to isolate a pure chemical agent from its natural origin. This entailed a step-by-step separation of extracted components based on differences in their physicochemical properties, and assessing all their biological activity. The extracted components may, for example, be fractionated by dry column flash chromatography on Si gel using hexane/CH2Cl2/ethyl acetate and mixtures of increasing polarity to yield different fractions. The sample is then degassed by ultrasonication to yield an insoluble solid, which solid is then filtered. The sample may then be subjected to high performance liquid chromatography (HPLC) using a column Phenomenex Luna™ C18, 5 µm, 2×50 mm; eluent, acetonitrile with 0.05% MeOH to confirm the presence of the various fractions.

At step 40, bioactivity of the extracts were verified by an anticancer cell proliferation assay as described above. This identified the bioactive cannabinoids from all the supercritical fluid extracts (SFE). As reported previously, the identified cannabis-based cannabinoid extracts showed activity against several cancer cell lines including brain, breast, Kaposi sarcoma, leukemia, lung, melanoma, ovarian, pancreatic, colon and prostate cancer.

The next step was to identify the cannabis-based cannabinoid constituents responsible for the observed anti-cancer and anti-inflammatory activities and to further isolate them.

At step 50 Nuclear Magnetic Resonance Spectroscopy and mass spectrometry (NMR/MS) was performed and the interpreted spectra were consistent with cannabis-based cannabinoid compositions CBD as identified above, and as shown in step 60.

An alternative method of method of preparing cannabidiol from plant material is shown in U.S. Published Patent Application 20060167283.

Synthesis of Cannabis Cannabinoids

Synthetic forms of CBD are commercially available (e.g. from Sigma Corp.) but are prohibitively expensive. Furthermore, HPLC analysis reveals the presence of significant amounts of THC (typically around 1%) in the commercially available preparations of cannabidiol. The synthesis of cannabidiol has been accomplished by several research groups. [Petrzilka T, Haefliger W, Sikemeier C, Ohloff G, Eschenmoser A, *Synthese und Chiralität des(−)-Cannabidiols*, Helv. Chim. Acta. 50 (1997) doi:10.1002/hlca.19670500235. PMID 5587099; Jump up ^ Gaoni Y, Mechoulam R (1985). *Boron Trifluoride Etherate On Alumuna—A Modified Lewis Acid Reagent. An Improved Synthesis Of Cannabidiol*, Tetrahedron Letters. 26(8): 1083-1086. doi:10.1016/S0040-4039(00)98518-6; Kobayashi Y, Takeuchi A, Wang Y G (2006), *Synthesis Of Cannabidiols Via Alkenylation Of Cyclohexenyl Monoacetate*, Org. Lett. 8 (13): 2699-2702. doi:10.1021/ol60692h. PMID 16774235]

It should now be apparent that the above-described invention provides a pharmaceutical composition for the prevention and treatment of pathogenic viruses (particularly those causing viral hepatic related conditions such as hepatitis B and C), and most particularly for hepatitis C virus (HCV) infection, using a cannabinoid-based pharmaceutical composition having a CBD molecular formula or a pharmaceutically acceptable salt thereof. Also disclosed are a method for the prevention and treatment of disease using the specific cannabis-based cannabinoid pharmaceutical compositions and a method for isolating the cannabis-based cannabinoid pharmaceutical compositions from raw plant material for the specific cannabis-based cannabinoid pharmaceutical compositions.

It is to be understood, therefore, that the invention may be practiced otherwise than as specifically set forth in the appended claims.

We claim:

1. A method of treating hepatitis C in a human subject comprising administering a composition comprising a therapeutically-effective dose of cannabidiol (CBD) to said subject.

2. The method of treating hepatitis C according to claim 1, wherein the composition is at least 98% (w/w) CBD.

3. The method of treating hepatitis C according to claim 1, wherein the step of administering a therapeutically-effective dose of CBD to said subject comprises administering a therapeutically effective dose of CBD ranging from 5 mg/kg/day to 25 mg/kg/day.

4. The method of treating hepatitis C according to claim 1, wherein the step of administering a therapeutically-effective dose of CBD to said subject comprises administering a therapeutically effective dose of CBD of at least 400 mg per day.

5. The method of treating hepatitis C according to claim 2, wherein the CBD is extracted from a plant.

6. The method of treating hepatitis C according to claim 1, wherein the CBD has a structure of the following formula or a pharmaceutically acceptable salt thereof:

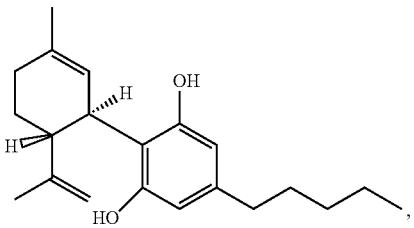 [SMILES: C=C(C)[C@@H]1CCC(C)=C[C@H]1c1c(O)cc(CCCCC)cc1O]

7. A method of treating hepatitis C in a human subject comprising the steps of:
   determining that a subject has hepatitis C; and
   providing to the subject an amount of CBD effective for the treatment of the hepatitis C.

8. A method of treating hepatitis C, comprising:
   determining a therapeutically-effective amount of a compound having the specific chemical structure shown below:

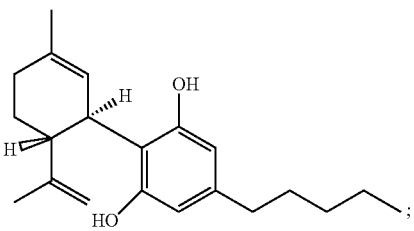 [SMILES: C=C(C)[C@@H]1CCC(C)=C[C@H]1c1c(O)cc(CCCCC)cc1O]

and
   administering a composition comprising the compound to a human subject for the treatment of hepatitis C virus.

9. The method of treating hepatitis C of claim 8, wherein the composition comprises at least at least 98% (w/w) of the compound.

10. The method of treating hepatitis C of claim 8, wherein the step of administering a composition comprising the compound comprises administering a therapeutically effective dose of said compound ranging from 5 mg/kg/day to 25 mg/kg/day.

11. The method of treating hepatitis C of claim 8 wherein the step of administering a composition comprising the compound comprises administering a therapeutically effective dose of the compound of at least 400 mg per day.

12. The method of treating hepatitis C of claim 8, wherein the step of administering a composition comprising the compound comprises administering a therapeutically effective dose of the compound via a route selected from a group consisting of: a topical route, an oral route, and a rectal route.

13. The method of treating hepatitis C of claim 8, wherein the step of administering a composition comprising the compound comprises injecting the composition into a location of the human subject's body selected from the group consisting of: a vein, an epidural muscle, a subcutaneous location, an intrauterine location, and an intracerebroventricular location.

14. The method of treating hepatitis C of claim 8, further comprising:
   selecting a dose of the compound based on at least one factor selected from a group consisting of: the human subject's body weight, a form of the composition, a route of administration of the composition, and a duration of administration;
   wherein the step of administering a composition comprising the compound comprises administering the selected dose of the compound.

15. The method of treating hepatitis C of claim 8, wherein the composition comprises a carrier substance selected from a group consisting of: lactose, dextrose, sucrose, sorbitol, mannitol, xylitol, erythritol, maltitol, starches, gum acacia, alginate, gelatin, calcium phosphate, calcium silicate, cellulose, methyl cellulose, microcrystalline cellulose, polyvinylpyrrolidone, water, methyl benzoate, propyl benzoate, talc, magnesium stearate, and mineral oil.

16. The method of treating hepatitis C of claim 8, wherein the composition is formulated in a form selected from a group consisting of: a powder, a granule, a tablet, a capsule, a suspension, an emulsion, a syrup, an aerosol, a suppository, and an injectable solution.

* * * * *